(12) United States Patent
Damiano et al.

(10) Patent No.: US 12,089,827 B2
(45) Date of Patent: *Sep. 17, 2024

(54) SYSTEMS AND METHODS FOR STORAGE OF STERILE DEVICES

(71) Applicant: Boston Scientific Scimed, Inc., Maple Grove, MN (US)

(72) Inventors: Bud Louis Damiano, Leominster, MA (US); Ryan Neil Watson, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/354,137

(22) Filed: Jul. 18, 2023

(65) Prior Publication Data

US 2023/0355222 A1   Nov. 9, 2023

Related U.S. Application Data

(63) Continuation of application No. 16/403,920, filed on May 6, 2019, now Pat. No. 11,744,564.

(60) Provisional application No. 62/669,584, filed on May 10, 2018.

(51) Int. Cl.
| | |
|---|---|
| *A61B 50/30* | (2016.01) |
| *A61B 17/00* | (2006.01) |
| *A61B 50/33* | (2016.01) |
| *A61L 2/20* | (2006.01) |
| *A61M 39/20* | (2006.01) |
| *A61B 50/00* | (2016.01) |
| *A61M 25/00* | (2006.01) |

(52) U.S. Cl.
CPC ........ *A61B 17/00234* (2013.01); *A61B 50/33* (2016.02); *A61L 2/20* (2013.01); *A61M 39/20* (2013.01); *A61B 2017/00362* (2013.01); *A61B 2017/0042* (2013.01); *A61B 2050/002* (2016.02); *A61B 2050/0066* (2016.02); *A61B 2050/0083* (2016.02); *A61M 25/002* (2013.01)

(58) Field of Classification Search
CPC ............. A61B 50/33; A61B 2050/002; A61B 17/00234; A61B 2050/0066; A61B 2050/0083; A61B 2017/0042; A61B 2017/00362; A61M 25/002; A61M 39/20
USPC .......................... 206/438, 363; 422/200, 300
See application file for complete search history.

(56) References Cited

U.S. PATENT DOCUMENTS

| | | | | |
|---|---|---|---|---|
| 3,685,248 A | * | 8/1972 | Godelaine | B65B 3/003 53/425 |
| 3,690,315 A | * | 9/1972 | Chittenden | A61M 1/70 604/129 |
| 5,881,536 A | | 3/1999 | Muller-Wille et al. | |
| 5,997,811 A | * | 12/1999 | Esposito | A61B 50/30 422/1 |

(Continued)

*Primary Examiner* — Steven A. Reynolds
(74) *Attorney, Agent, or Firm* — Bookoff McAndrews PLLC

(57) ABSTRACT

In one example, a sterile container may include a tray having a plurality of walls at least partially defining a cavity. At least one of the plurality of walls may include an opening extending therethrough. The sterile container may further include a seal structure coupled to the tray. At least a portion of the seal structure may be received within the opening of the at least one of the plurality of walls. Additionally, the sterile container may include an extension structure coupled to the seal structure.

18 Claims, 2 Drawing Sheets

(56) References Cited

U.S. PATENT DOCUMENTS

| | | |
|---|---|---|
| 8,747,739 B2 | 6/2014 | Parker et al. |
| 9,149,939 B2 | 10/2015 | Zambaux |
| 10,555,872 B1 | 2/2020 | Thorne |
| 2003/0205029 A1 | 11/2003 | Chapolini et al. |
| 2012/0255879 A1 | 10/2012 | Gillespie |
| 2015/0144514 A1 | 5/2015 | Brennan et al. |

* cited by examiner

SYSTEMS AND METHODS FOR STORAGE OF STERILE DEVICES

CROSS-REFERENCE TO RELATED APPLICATIONS

This patent application is a continuation of U.S. Application Ser. No. 16/403,920, filed on May 6, 2019, which claims the benefit of priority under 35 U.S.C. § 119 to U.S. Provisional Patent Application No. 62/669,584, filed on May 10, 2018, each of which is herein incorporated by reference in its entirety.

TECHNICAL FIELD

The present disclosure relates generally to storage of sterile devices. More specifically, the present disclosure relates to devices and methods for storing one or more sterile medical devices and/or medical insertion devices.

BACKGROUND

Medical containers or trays are used to provide sterile storage and protection for medical devices and/or medical insertion devices. By sealing the medical device and/or medical insertion device within a tray via a commercial tray sealer, the medical device and/or medical insertion device is maintained in a sterile environment to protect the medical device and/or medical insertion device from germs and other pollutants. As certain medical devices and/or medical insertion devices include both a handle and a relatively long shaft extending therefrom, such trays often are required to be long enough to accommodate both the handle and the shaft in a sterile environment without damage. As such, many trays arranged to accommodate such long devices are too large to be sealed by generally available commercial tray sealers. Accordingly, medical facilities are often required to invest in additional specialized equipment to seal such medical devices and/or medical insertion devices within a tray. Additionally, because of their size, such trays are both expensive to manufacture and cumbersome to carry in the operating room.

SUMMARY

Examples of the present disclosure relate to, among other things, sterile trays or containers for medical devices and/or medical insertion devices. Each of the examples disclosed herein may include one or more of the features described in connection with any of the other disclosed examples.

In one example, a sterile container may include a tray having a plurality of walls at least partially defining a cavity. At least one of the plurality of walls may include an opening extending therethrough. The sterile container may further include a seal structure coupled to the tray. At least a portion of the seal structure may be received within the opening of the at least one of the plurality of walls. Additionally, the sterile container may include an extension structure coupled to the seal structure.

Examples of the sterile container may include any one or more of the following features. The seal structure may include a first component located on a first side of the at least one wall of the plurality of walls, and a second component located on a second side of the at least one wall of the plurality of walls, and the second side may be opposite the first side. The first component may include a hub and a stem received within the opening of the at least one wall of the plurality of walls. The stem may include at least one of groove or a threaded surface. The second component may include a hub and a lumen extending therethrough. At least a portion of the first component may be received within the lumen of the second component. The stem may include the groove, and the second component may include at least one snap feature arranged for receipt within the groove. The stem may include the threaded surface, and the lumen of the second component may include a threaded surface for engagement with the threaded surface of the stem. At least one seal may be positioned between the at least one wall of the plurality of walls and the seal structure. The at least one seal may be an adhesive. The extension structure may include a first end coupled to the seal structure and a second end opposite the first end, and the second end may include a cap. The cap may include a sterile filter. The extension structure may be between about 40 inches and about 45 inches long. The sterile container may include a Tyvek lid. The tray may be generally rectangular and a cross-sectional shape of the extension structure may be circular.

In a further arrangement, a sterile system may include a medical insertion device having a handle and a shaft coupled to the handle. The sterile system may further include a sterile container including a tray having a plurality of walls at least partially defining a cavity. At least one of the plurality of walls may include an opening extending therethrough and the handle of the medical insertion device may be positioned within the cavity. The sterile system may further include a seal structure coupled to the tray and an extension structure coupled to the seal structure. The shaft of the medical insertion device may be received within at least a portion of each of the seal structure and the extension structure.

Examples of the sterile system may include any one or more of the following features. The extension structure may include a first end coupled to the seal structure and a second end opposite the first end, wherein the second end includes a cap, and wherein the cap includes a sterile filter. The seal structure may include a first component located on a first side of the at least one wall of the plurality of walls, and a second component located on a second side of the at least one wall of the plurality of walls, in which the second side is opposite the first side. At least a portion of the first component may be received within the lumen of the second component. The first component may include a hub and a stem, the stem may be received within the opening of the at least one wall of the plurality of walls, and the stem may include at least one of groove or a threaded surface. The second component may include a hub and a lumen extending therethrough. At least one seal may be positioned between the at least one wall of the plurality of walls and the seal structure, and the at least one seal may be an adhesive.

In a further example, a method for maintaining sterility of a medical insertion device may include positioning a handle of a medical insertion device within a thermoformed tray. The method may further include extending a shaft of the insertion device through a seal structure coupled to the thermoformed tray and into an extension structure of the thermoformed tray. Additionally, the method may include sealing a cavity of the thermoformed tray via a Tyvek lid.

In a further arrangement, the method may include extending the shaft of the medical insertion device through a seal structure including extending the shaft of the medical insertion device through a first component of the seal structure located on a first side of a wall of the thermoformed tray and extending the shaft of the medical insertion device through a second component of the seal structure located on a second side of the wall opposite the first side.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to sterile trays and containers for medical devices and/or medical insertion devices for treating internal areas of a patient's body. Each of the sterile trays or containers described herein may include a seal structure for preventing contamination of a medical device and/or medical insertion device positioned therein.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or medical insertion device. When used herein, "proximal" refers to a position relatively closer to the exterior of the patient or closer to a medical professional using the medical device or medical insertion device. In contrast, "distal" refers to a position relatively farther away from the medical professional using the medical device or medical insertion device, or closer to the interior of the patient.

Figure 1:
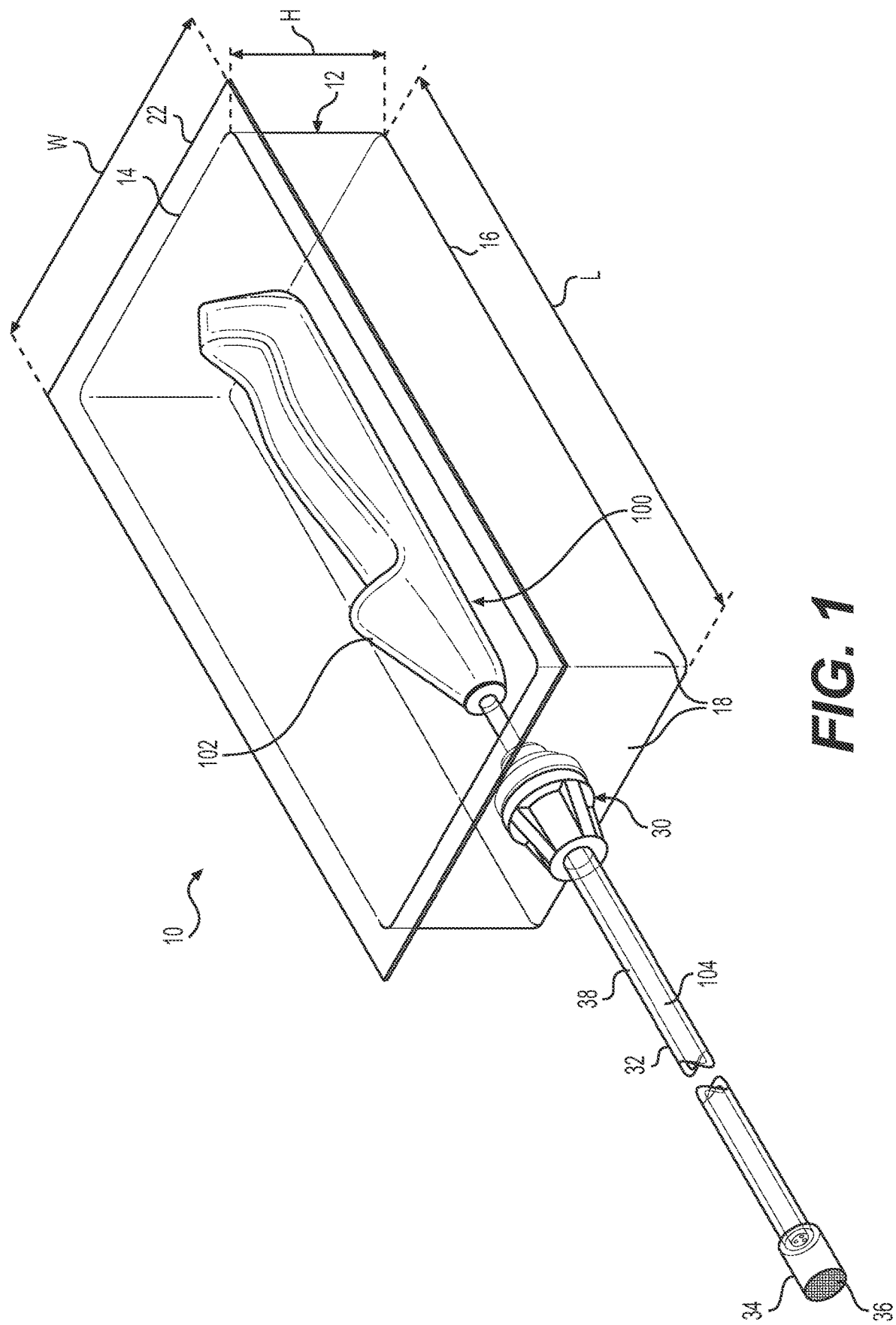
FIG. 1 illustrates an exemplary sterile container including an exemplary medical insertion device therein, according to the present disclosure.

FIG. 1 illustrates an exemplary sterile container 10 including an exemplary medical insertion device 100 therein. Container 10 includes a tray 12 defining a cavity 14. As shown, tray 12 may be generally rectangular, however, the disclosure is not so limited. Rather, tray 12 may have any appropriate shape, size, and/or arrangement to accommodate at least a portion of medical insertion device 100 (e.g., a handle 102 of medical insertion device 100). As will be described in further detail below, tray 12 may be sized so as to receive a handle 102 of an exemplary medical device 100, rather than the entirety of medical insertion device 100. In such a fashion, tray 12 may be significantly smaller than typical sterile trays.

With continuing reference to FIG. 1, tray 12 includes a first planar wall (e.g., a bottom or lower wall) 16 and a plurality (e.g., four) second planar walls (e.g., side walls) 18 extending orthogonally to first planar wall 16, and thereby defining cavity 14. In other arrangements, however, second planar walls 18 may extend non-orthogonally to first planar wall 16. Tray 12, including walls 16 and 18, may be thermoformed of any appropriate material, such as, for example, high impact polystyrene (HIPS), polyethylene terephthalate glycol (PETG), polycarbonate (PC), polyvinyl chloride (PVC), high-density polyethylene, low-density polyethylene, etc.

At least one of such walls 16 and 18 may include an opening 20 (FIGS. 2 and 3) within which a seal structure 30 (e.g., a seal port) may be arranged. As will be described in further detail below, seal structure 30 may provide a sterile connection between an extension structure 32 (e.g., a tube, pipe, sheath, or the like) and tray 12. Extension structure 32 may include any appropriate material such as, for example, polymers or the like, acrylonitrile butadiene styrene (ABS), nylon, polycarbonate (PC), polypropylene (PP), polyethylene (PE), etc. Additionally, extension structure 32 may have any appropriate length so as to accommodate a shaft 104 of insertion device 100 therein. For example, shaft 104 may be about 39 inches to about 42 inches long, and as such, extension structure 32 may be about 40 inches to about 45 inches long. In other arrangements, extension structure 32 may be equal to or greater than 20 inches long. Further, extension structure 32 may have any appropriate cross-sectional shape (e.g., circular, ovular, polygonal, or irregular).

As shown, a distal end (e.g., an end opposite that of tray 12) of extension structure 32 may be covered via a cap 34. Cap 34 may be secured to the distal end of extension structure 32 in any appropriate manner such as, for example, adhesive bonding. A distal end face of cap 34 may include a sterile filter 36. Sterile filter 36 may comprise a filter media of tightly woven, knit, or mesh filaments having a porosity sufficient to permit venting of the medical insertion device 100 within cavity 14 while preventing ingress of germs or microbes therethrough, thus maintaining the sterile environment of tray 12. Moreover, filter 36 may also permit a sterilant, e.g., vaporized hydrogen peroxide, or Ethelene Oxide to enter into and exit from extension structure 32 and/or cavity 14. While filter 36 is described and depicted on the distal end face of cap 34, in other arrangements, filter 36 may be positioned at or along any one or more portions of cap 34 (e.g., a side wall of cap 34). Filter 36 may include any appropriate materials, such as, for example, flat filter material, molded porous material, Tyvek, paper, etc.

In use, at least a portion, e.g., a handle, of medical insertion device 100 may be placed within tray 12. Insertion device 100 may include any device configured to allow a user to access and view internal areas of a subject's body such as, for example, an endoscope, a ureteroscope, a hysteroscope, a uteroscope, a bronchoscope, a cystoscope, and similar devices. Optionally, tray 12 may be arranged to receive a medical device (e.g., a medical tool such as forceps, graspers, snares, laser fibers, scissors, or the like, not shown.) In use, handle 102 of medical insertion device 100 may be arranged within cavity 14 of tray 12, while shaft 104 of medical insertion device 100 may be passed through seal structure 30 and into a lumen 38 of extension structure 32.

Following placement of medical insertion device 100 (and/or a medical device) within tray 12, tray 12 may be sealed with lid 22. Lid 22 may include any appropriate material such as, for example, flash-spun high-density polyethylene fibers (Tyvek®). Lid 22 may be attached to tray 12 so as to seal cavity 14 in any appropriate fashion such as, for example, via a commercial tray sealer. That is, since tray 12 does not receive the entirety of medical insertion device 100 within cavity 14, tray 12 does not require specialized equipment for sealing tray 12 and the contents therein. Additionally, as tray 12 is significantly smaller than the entirety of insertion device 100, tray 12 may be less expensive to manufacture and may be more environmentally friendly. Once sealed within container 10, a sterility of insertion device 100 may be maintained until ready for use by a medical professional. Moreover, filter 36 may allow for a sterilization process to sterilize the distal end of insertion device 100.

Figure 2:
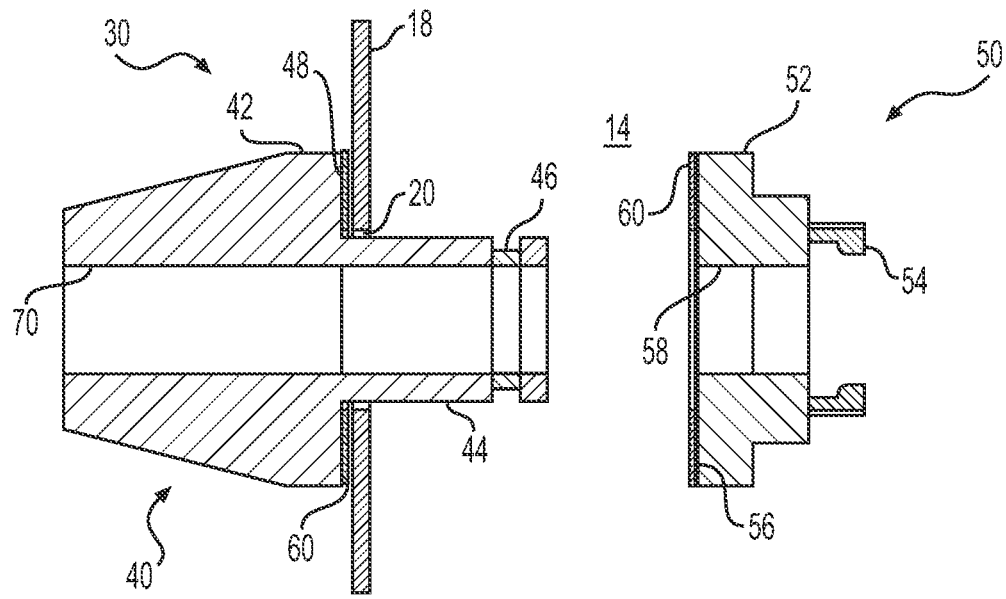
FIG. 2 illustrates an exemplary seal structure according to aspects of the present disclosure.

FIG. 2 illustrates an exploded cross-sectional view of the exemplary seal structure 30. As shown, seal structure 30 includes a first (e.g., outer, external) component 40 and a second component 50. First component 40 includes a hub 42 positioned on an exterior surface of wall 18 (e.g., a surface of wall 18 that is exposed to a non-sterile environment) and a stem 44 extending through opening 20 and into cavity 14. As shown, stem 44 includes a recess, channel, or groove 46. Groove 46 is arranged to accommodate a snap feature 54 of second component 50, as will be described in further detail below. As shown, hub 42 of first component 40 includes a wall-facing surface 48 facing wall 18. In order to maintain sterility of container 10, a first seal 60 may be positioned between wall-facing surface 48 and wall 18. First seal 60 may comprise any one or more of an O-ring or an adhesive, as will be described in further detail below. An end of extension structure 32 (FIG. 1) opposite that of cap 34 may be secured to a surface of first component 40. For example, hub 42 may include a passage, through bore, or lumen defined by an interior surface 70. The end of extension structure 32 may be adhesively bonded with surface 70 within one or both of hub 42 and stem 44 of first component 40. Optionally, the end of extension structure 32 may be secured to first component 40 without adhesives. In such a case, extension structure 32 may be secured to first component 40 via any appropriate sterile connection mechanism (e.g., an O-ring or the like).

Second component 50 includes a hub 52 positioned on an interior surface of wall 18 (e.g., a surface of wall 18 that is exposed to cavity 14) and one or more snap features 54 extending therefrom. As shown, hub 52 of second component 50 includes a wall-facing surface 56 facing wall 18. In order to maintain sterility of container 10, a second seal 60 may be positioned between wall-facing surface 56 and wall 18. Second seal 60 may comprise any one or more of an O-ring or an adhesive, as will be described in further detail below. Additionally, second component 50 may include a passage, through bore, or lumen defined by an interior surface 58. Upon assembly, stem 44 of first component 40 may be passed through the lumen until the one or more snap features 54 of second component 50 are received within groove 46, thereby securing first component 40 to second component 50 on opposite sides of wall 18. That is, upon assembly, wall 18 of tray 12 is sandwiched between first component 40 and second component 50.

Figure 3:
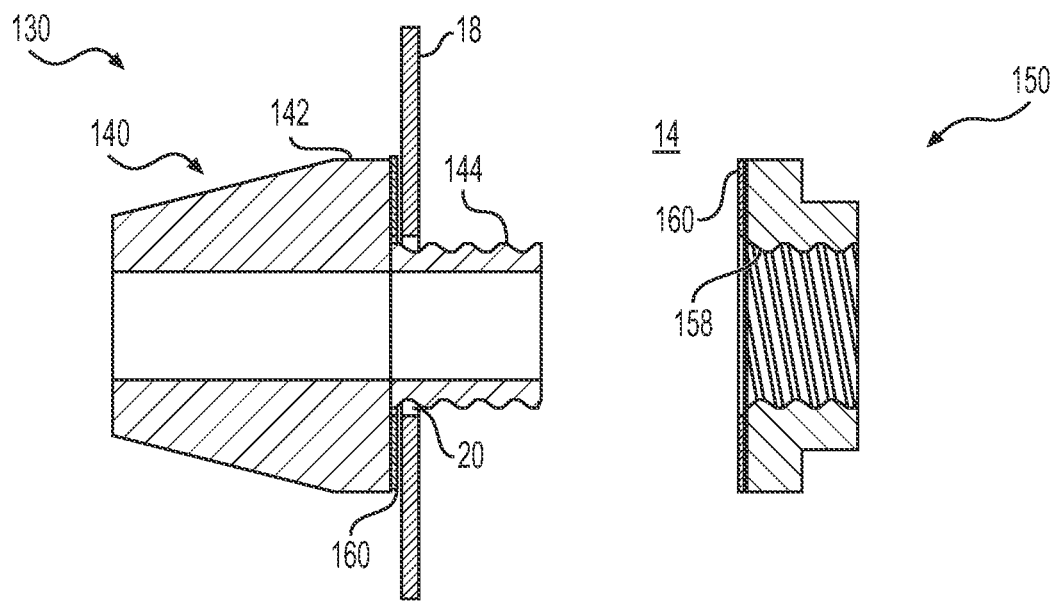
FIG. 3 illustrates an alternative exemplary seal structure according to additional aspects of the present disclosure.

FIG. 3 illustrates an exploded cross-sectional view of an exemplary seal structure 130, according to a further aspect. Seal structure 130 includes similar features to that of seal 30, where like components are indicated with the same reference numeral incremented by 100. For example, seal structure 130 includes a first component 140 including a hub 142 and a stem 144. Additionally, seal structure 130 includes a second component 150 including a passage, bore, or lumen defined by an interior surface 158. In contrast to seal structure 30, however, stem 144 is threaded and does not include groove 46. Additionally, interior surface 158 of second component 150 is threaded and does not include one or more snap features 54. Accordingly, upon assembly of the arrangement shown in FIG. 3, stem 144 of first component 140 may be passed through opening 20 of wall 18, and threadably engaged with second component 150 via threads of stem 144 and threads of inner surface 158, thereby securing first component 140 to second component 150 on opposite sides of wall 18. That is, upon assembly, wall 18 of tray 12 is sandwiched between first component 140 and second component 150. In addition, seals 160 may be positioned between first component 140 and second component 150 on opposite sides of wall 18. Similarly to seals 60, seals 160 may comprise any one or more of an O-ring or an adhesive.

It is understood that any of the adhesives described herein may include one or more of an ultra-violent cured adhesive, epoxy, cyanoacrylate, or silicone. Additionally, it is understood that in arrangements in which first and second seals 60, 160 comprise an adhesive itself, no additional mechanical fastening (e.g., groove 46 and snap features 54, or threading) is required between first component 40, 140 and second component 50, 150 of seal structure 30, 130. Rather, the adhesive of each of the first and second seals 60, 160 may be sufficient to secure the first component 40, 140 and the second component 50, 150 to opposite sides of wall 18.

While principles of the present disclosure are described herein with reference to illustrative examples for particular applications, it should be understood that the disclosure is not limited thereto. For example, in some arrangements, a seal structure may include a first component and a second component coupled together via a friction fit (e.g., without a snap-fitting or screw thread engagement). Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A sterile container, comprising:
   a tray having a plurality of walls at least partially defining a cavity, a wall of the plurality of walls including an opening therethrough;
   a seal structure, a portion of the seal structure being received within the opening;
   an extension structure having a proximal end coupled to the seal structure and a distal end, the extension structure defining a lumen between the proximal end and the distal end; and
   a cap secured to the distal end of the extension structure, the cap including a sterile filter at a distalmost face of the cap;
   wherein the lumen is in communication with the cavity, the lumen being configured to receive a shaft of a medical device and the cavity being configured to receive a handle of the medical device.

2. The sterile container of claim 1, wherein the sterile filter has a porosity that permits venting while preventing ingress of microbes into the sterile container.

3. The sterile container of claim 1, further comprising a lid coupled to the tray to seal the cavity.

4. The sterile container of claim 1, wherein the seal structure includes a first component on a first side of the wall that includes the opening, the proximal end of the extension structure being coupled to the first component.

5. The sterile container of claim 4, wherein the seal structure includes a seal between the first component and the first side of the wall.

6. The sterile container of claim 5, wherein the seal comprises an O-ring or an adhesive.

7. The sterile container of claim 4, wherein the seal structure includes a second component on a second side of the wall that includes the opening opposite the first side.

8. The sterile container of claim 7, wherein the first component, the second component, or both the first component and the second component are sealed to the wall with an adhesive.

9. The sterile container of claim 1, wherein the extension structure is at least 20 inches long.

10. The sterile container of claim 1, wherein the plurality of walls of the tray are thermoformed.

11. A sterile container comprising:
   a tray having a plurality of walls at least partially defining a cavity;
   a lid coupled to the tray to seal the cavity;
   a seal structure coupled to a wall of the plurality of walls of the tray;
   an extension structure defining a lumen therethrough, wherein a proximal end of the extension structure is coupled to the seal structure; and
   a cap secured to a distal end of the extension structure, the cap including a sterile filter at a distalmost face of the cap;
   wherein the lumen of the extension structure is configured to receive a shaft of a medical insertion device, and the cavity of the tray is configured to receive a handle of the medical insertion device.

12. The sterile container of claim 11, wherein the sterile container houses the medical insertion device, the lumen of the extension structure receiving the shaft of the medical insertion device and the cavity of the tray receiving the handle of the medical insertion device.

13. The sterile container of claim 11, wherein the sterile filter has a porosity that permits venting while preventing ingress of microbes into the sterile container.

14. The sterile container of claim 11, wherein the seal structure includes a first component on an outer side of a wall of the tray and a second component on an inner side of the wall of the tray, each of the first component and the second component being sealed to the wall with an adhesive or an O-ring.

15. The sterile container of claim 11, wherein the plurality of walls of the tray are thermoformed.

16. A sterile container, comprising:
   a tray having a plurality of walls at least partially defining a cavity, a wall of the plurality of walls including an opening therethrough;
   a seal structure, a portion of the seal structure being received within the opening; and
   an extension structure having a proximal end coupled to the seal structure and a distal end that includes a sterile filter that permits venting while preventing ingress of microbes into the sterile container;
   wherein the extension structure defines a lumen between the proximal end and the distal end, the lumen being in communication with the cavity; and
   wherein the sterile container houses a medical insertion device that comprises a handle coupled to a shaft, the lumen of the extension structure receiving the shaft of the medical insertion device and the cavity of the tray receiving
   the handle of the medical insertion device.

17. The sterile container of claim 16, wherein the extension structure includes a cap, and a distal end face of the cap includes the sterile filter, and wherein a distal end of the shaft is proximal to the sterile filter.

18. The sterile container of claim 16, wherein the seal structure includes a first component on a first side of the wall that includes the opening and a second component on a second side of the wall that includes the opening, each of the first component and the second component being sealed to the wall.

* * * * *